US005912720A

United States Patent [19]
Berger et al.

[11] Patent Number: 5,912,720
[45] Date of Patent: Jun. 15, 1999

[54] TECHNIQUE FOR CREATING AN OPHTHALMIC AUGMENTED REALITY ENVIRONMENT

[75] Inventors: Jeffrey W. Berger, Cherry Hill, N.J.; Michael E. Leventon, Pittsburgh, Pa.; Ron Kikinis, Brookline, Mass.

[73] Assignee: The Trustees of the University of Pennsylvania

[21] Appl. No.: 09/022,878

[22] Filed: Feb. 12, 1998

Related U.S. Application Data

[60] Provisional application No. 60/037,985, Feb. 13, 1997.

[51] Int. Cl.$^6$ ..................................................... A61B 3/14
[52] U.S. Cl. .......................................................... 351/206
[58] Field of Search ................................... 351/205, 206, 351/208, 209, 210, 215, 221, 246

[56] References Cited

U.S. PATENT DOCUMENTS

| | | | |
|---|---|---|---|
| 3,893,447 | 7/1975 | Hochheimer et al. | 351/206 |
| 5,360,010 | 11/1994 | Applegate | 351/221 |
| 5,394,199 | 2/1995 | Flower | 351/215 |

OTHER PUBLICATIONS

Canny, "A Computational Approach to Edge Detection", *IEEE Trans. Pat. Anal. Mach. Intel.*, vol. 8, No. 6, pp. 679–698 (Nov. 1986).

Grimson, et al., "An Automatic Registration Method for Frameless Stereotaxy, Image Guided Surgery, and Enhanced Reality Visualization", *IEEE Trans. Med Imaging*, vol. 15, No. 129, pp. 0–27 (Feb. 22, 1996).

Huttenlocher, et al. "Comparing Images Using the Hausdorff Distance", *IEEE Trans. Pat. Anal. Mach. Intel.*, vol. 15, No. 9, pp. 850–863 (Sep. 1993).

Maguire, et al., "The Influence of Treatment Extent on the Visual Acuity of Eyes Treated With Krypton Laser for Juxtafoveal Choroidal Neovascularization", *Arch Opthalmol*, vol. 113, pp. 190–194 (Feb. 1995).

Neely, "How to Be More Successful with Laser Photocoagulation", *Review of Ophthalmology*, pp. 103–109 (Jun. 1996).

Rucklidge, "Locating Objects Using the Hausdorff Distance", *IEEE Int. Conf. Comp. Vision*, pp. 457–464 (1995).

Bajura, et al., "Merging Virtual Objects with the Real World: Seeing Ultrasound Imagery Within the Patient", *Computer Graphics* 26(2): 203–210, (1992).

Barrett, et al., "Computer–Aided Retinal Photocoagulation System", *Journal of Biomedical Optics*, vol. 1, No. 1, pp. 83–91 (Jan. 1996).

Barrett, et al., "Digital tracking and control of retinal images", *Optical Engineering*, vol. 33, No. 1, pp. 150–159 (Jan. 1994).

Becker, et al., "Real–Time Image Processing Algorithms for an Automated Retinal Laser Surgery System", *IEEE*, 2nd Int. Conf. Im. Proc., pp. 426–429 (1995).

(List continued on next page.)

*Primary Examiner*—George Manuel
*Attorney, Agent, or Firm*—Woodcock Washburn Kurtz, Mackiewicz & Norris, LLP

[57] ABSTRACT

An ophthalmic augmented reality environment is developed in order to allow for (a) more precise laser treatment for ophthalmic diseases, (b) teaching, (c) telemedicine, and (d) real-time image measurement, analysis, and comparison. A preferred embodiment of the system is designed around a standard slit-lamp biomicroscope. The microscope is interfaced to a CCD camera, and the image is sent to a video capture board. A single computer workstation coordinates image capture, registration, and display. The captured image is registered with previously stored, montaged photographic and/or angiographic data, with superposition facilitated by fundus-landmark-based fast registration algorithms. The computer then drives a high intensity, VGA resolution video display with adjustable brightness and contrast attached to one of the oculars of the slit-lamp biomicroscope.

35 Claims, 9 Drawing Sheets

OTHER PUBLICATIONS

Chamberlin, et al., "The Use of Fundus Photographs and Fluorescein Angiograms in the Identification and Treatment of Choroidal Neovascularization in the Macular Photocoagulation Study", *Ophthalmology*, vol. 96, No. 10, pp. 1526–1534 (Oct. 1989).

Cideciyan, "Registration of Ocular Fundus Images", *IEEE Engineering in Medicine and Biology*, pp. 52–58 (Jan./Feb. 1995).

Edwards, et al., "Neurosurgical Guidance Using the Stereo Microscope", *Proc. First Int. Conf. Computer Vision, Virutal Reality and Robotics in Medicine*, Nice, France, pp. 555–564.

Gleason, et al., "Video Registration Virtual Reality for Nonlinkage Stereotactic Surgery", *Streotact Funct Neurosurg*, vol. 63, pp. 139–143 (1994).

Maguire, et al., "The Influence of Treatment Extent on the Visual Acuity of Eyes Treated with Krypton Laser for Juxtafoveal Choroidal Neovascularization", *Arch Ophthalmol*, vol. 113, pp. 190–194 (Feb. 1995).

Mahurkar, et al., "Constructing Retinal Fundus Photomontages", *Investigative Ophthalmology & Visual Science*, vol. 37, No. 8, pp. 1675–1683.

Markow, et al., "Real–Time Algorithm for Retinal Tracking", *IEEE*, vol. 40, No. 12, pp. 1269–1280, (Dec. 1993).

O'Toole, et al., "Image Overlay for Surgical Enhancement and Telemedicine", *Interactive Technology & The New Paradigm for Healthcare*, Chapter 42, pp. 271–272 (1995).

Szeliski, "Image Mosaicing for Tele–Reality Applications", *IEEE*, Proc. 2nd IEEE Workshop Applications of Computer Vision, Sarasota, FL pp. 44–53 (1994).

Tuceryan, et al., "Calibration Requirements and Procedures for a Monitor–Based Augmented Reality System", *IEEE*, vol. 1, No. 3, pp. 255–273 (Sep. 1995).

Uenohara, et al., "Vision–Based Object Registration for Real–Time Image Overlay", *Proc. 1st Int. Conf. Comp. Vision, Virtual Reality and Robotics in Medicine*, Nice, France, pp. 13–22 (1995).

Williamson, et al., "Telemedicine and computers in diabetic retinopathy screening", *British Journal of Ophthalmology*, vol. 82, pp. 5–6 (1998).

TECHNIQUE FOR CREATING AN OPHTHALMIC AUGMENTED REALITY ENVIRONMENT

This application claims benefit of Provisional Ser. No. 60/037,985, filed Feb. 13, 1997.

BACKGROUND OF THE INVENTION

1. Field of the Invention

The present invention relates to a technique of creating a computer-vision-enabled ophthalmic augmented reality environment for the diagnosis and treatment of eye diseases, and more particularly, to a technique for superimposing present and previous images to aid in the recognition and treatment of diseased tissue in the eye. The ophthalmic augmented reality platform also serves as a paradigm for telecollaboration, telemedicine, and teaching.

2. Description of the Prior Art

Diabetic macular edema and age-related macular degeneration (AMD) are the two major causes of visual loss in developed countries. While laser therapy for these and other diseases has prevented loss of visual function in many individuals, disease progression and visual loss following suboptimal treatment is common. For AMD, there is unambiguous evidence that incomplete laser photocoagulation of the border of a choroidal neovascular lesion is associated with an increased risk for further visual loss, while treatment beyond the borders unnecessarily destroys viable, central photoreceptors, further degrading visual function.

As a concrete example, in eyes with juxtafoveal choroidal neovascularization (CNV) secondary to ocular histoplasmosis, only 5% of eyes with laser treatment that covered the foveal side of the lesion with a narrow ($<100\mu$) treatment border suffered severe visual acuity loss, while approximately 25% of eyes with either some of the foveal side untreated, or a wide border of treatment on the foveal side suffered severe visual loss. Macular Photocoagulation Study Group, "The Influence of Treatment Extent on the Visual Acuity of Eyes Treated With Krypton Laser For Juxtafoveal Choroidal Neovascularization," *Arch. Ophthalmol.*, Vol. 113, pp. 190–194, 1995. Similar results have been reported for AMD.

Building on the recommendations proposed in Macular Photocoagulation Studies, clinicians generally attempt to correlate angiographic data with biomicroscopic images using crude manual, time-consuming, potentially error-prone methods. In a recent practical review in an article entitled "How to Be More Successful in Laser Photocoagulation," *Ophthal. Times*, pp. 103–108, 1996, Neely suggests that " . . . to assist you in treatment (of neovascular AMD), project an early frame of the fluorescein angiogram onto a viewing screen. Use the retinal vessels overlying the CNV lesion as landmarks. I suggest tracing an image of the CNV lesion and overlying vessels onto a sheet of onion skin paper. It takes a little extra time, but I find it helps to clarify the treatment area." Accordingly, precise identification of the treatment border during laser therapy by correlating the biomicroscopic image with fluorescein angiographic data should be beneficial for maximizing post-treatment visual function. Diagnosis and treatment relies on synthesizing clinical data derived from fundus biomicroscopy with angiographic data, but, at present, methods for correlating these data, and for direct guidance of laser therapy, do not exist.

As noted by O'Toole et al. in an article entitled "Image Overlay for Surgical Enhancement and Telemedicine," *Interactive Technology and the New Paradigm for Healthcare*, K. Morgan et al., editors, IOS Press, 1995, although there has been an explosive development of investigation into virtual reality applications in medicine, augmented reality applications might have a far greater utility, but have received much less attention. An early study by Bajura et al. reported in an article entitled "Merging Virtual Objects With the Real World: Seeing Ultrasound Imagery Within the Patient," *Computer Graphics*, Vol. 26, pp. 203–210, 1992, described the superposition of ultrasound images on the abdomen, using a position-tracked, see-through head mounted display. Recently, there has been great interest in neurosurgical applications of augmented reality. Specifically, it has been noted by Gleason et al. in an article entitled "Video Registration Virtual Reality for Non-linkage Stereotactic Surgery," *Stereotactic Funct. Neurosurgery*, Vol. 63, pp. 139–143, 194, by Edwards et al. in an article entitled "Neurosurgical Guidance Using the Stereo Microscope," *Proc. First Int. Conf. Computer Vision, Virtual Reality and Robotics in Medicine*, Nice, France, pp. 555–564, and by Grimson et al. in an article entitled "An Automatic Registration Method for Frameless Stereotaxy, Image Guided Surgery, and Enhanced Reality Visualization," *IEEE Trans. Medical Imaging*, Vol. 15, p. 129, 1996, that the intraoperative registration of CT, MR, and PET images on a living patient in the operating room may greatly facilitate surgical planning and execution. Typically, registration of the patient with the radiographic data is accomplished by tracking fiducial markers placed on the skin surface and tracking the position of the operating microscope. However, for ophthalmic applications, a technique is required that does not require fiducial markers or image tracking whereby a real-time image can be registered with a previously stored, montaged data set.

Moreover, methods for highly accurate real-time image comparison in AMD, cytomegalic virus retinitis, and diabetic retinopathy, for example, do not exist, and an appropriate platform for telecollaboration, telemedicine, and teaching has not heretofore been described. An ophthalmic augmented reality platform for this purpose is desired.

The present invention is directed to these needs in the art.

SUMMARY OF THE INVENTION

In view of the above-mentioned limitations in the prior art, the inventors have developed techniques for overlaying previously stored photographic and angiographic data on the real-time biomicroscopic slit-lamp fundus image in order to guide treatment for eye disease (for example, to better define and visualize the edges of choroidal neovascular membrane, and improve identification of focal areas of leakage in diabetic macular edema). In other words, the biomicroscopic fundus image is "augmented" in real time with available photographic and angiographic data. Text display and a "virtual pointer" are incorporated into the augmented reality display to facilitate teaching, telemedicine, and real-time measurement and image analysis. Such image superposition also allows for direct comparison with previous images to judge disease progression (for example, to judge progression or stability of AMD or cytomegalovirus retinitis-a common, blinding disease afflicting patients with acquired immuno-deficiency syndrome) and allows for real-time identification of prior treatment areas.

The invention is preferably implemented on a slit-lamp biomicroscope platform, which can be extended readily to an operating microscope based, an indirect ophthalmoscope based or fundus camera based system to facilitate correlative, teaching, and telemedicine applications in these environments.

The availability of formidable computation power has facilitated real-time image processing, allowing for investigation of useful augmented reality (AR) applications. The inventor's interest in developing a slit-lamp-biomicroscope-based AR environment are twofold. First, there is considerable interest in medical applications of AR for surgical planning and execution. The slit-lamp biomicroscope is an ideal model system for medical AR applications since (a) the slit-lamp fundus image is quasi-two-dimensional requiring less computational power than a three-dimensional application, and (b) the fundus landmarks are suitable targets for computer-vision-based recognition and tracking. Second, "augmenting" the fundus biomicroscopic view will allow for (a) more precise laser treatment for retinal diseases such as diabetic macular edema and age-related macular degeneration, (b) teaching, (c) telemedicine and telecollaboration, and (d) real-time image measurement and analysis.

Generally, the present invention relates to the design and implementation of an ophthalmic augmented reality environment, particularly for laser therapy of eye diseases. As known by those skilled in the art, laser therapy of eye diseases can result in severe visual loss due to the extension of the photocoagulation area beyond the diseased tissue, which destroys healthy viable tissue, or limitation of the treatment area, which fails to destroy the diseased tissue. The present invention thus specifically relates to a system and method for facilitating the accurate identification of diseased tissue by overlaying angiographic data and photographic images onto the real-time biomicroscopic fundus image. After calculating the best overlap of the photographic and angiographic images, the composite image is rendered visible. This technique of image overlay falls under the broad heading of "augmented reality" (AR) as used herein, which refers to the extraction and augmentation of real world images, as opposed to virtual reality, which refers to a computer constructed, synthetic environment. Potential advantages of an ophthalmic AR environment include more precise treatment for retinal diseases, teaching, telemedicine and telecollaboration, and real-time image measurement and comparison.

The fundus images are obtained by a standard ophthalmic slit-lamp biomicroscope which is interfaced to a CCD camera. The captured image is sent to a frame-grabber and digitizer. However, there are two issues regarding the ophthalmic AR environment, namely, determining the ideal overlap of the images and displaying the data. Determination of the relationships among various images is complicated by the potential absence of corresponding structures between the angiographic and photographic images, e.g., the features that are present in the photographic images may not appear in the angiographic images and vice versa. In addition, the images may not sample the same area of the retina and the images will differ in translation, rotation, magnification, and warp-related misalignment.

Accordingly, the first procedure of the method of the invention is to create a map of the posterior retina so that the precise position of the illumination beam can be subsequently tracked in real-time. One to seven partially overlapping photographic images are acquired with standard photographic techniques and merged to create a seamless mosaic, or photomontage. Second, stored photographic and angiographic data are registered (aligned spatially) with the photomontage to allow for rapid rendering of the graphical information simultaneous with tracking. The first two steps are performed in non-real-time using highly accurate Hausdorff-distance-based, polynomial warping, or elastic matching algorithms.

While the real-time augmented reality system of the invention is designed around the binocular slit-lamp biomicroscope, identical implementations are valid for a binocular operating microscope, a binocular indirect ophthalmoscope, or a monocular fundus camera. For the latter, images are acquired and rendered through the one eyepiece. For the slit-lamp binocular biomicroscope, a beamsplitter is attached to one eyepiece and interfaced to a CCD camera. The camera signal is sent to a framegrabber/digitizer on a personal computer. Template matching algorithms allow the position of the illuminated slit-lamp image to be determined relative to the previously stored photomontage.

Real-time registration may be implemented in software and/or hardware. Software methods rely on Hausdorff-distance or correlation based template matching. These algorithms may be made more efficient using image framegrabber boards with on board digital signal processing. The computer can then render the previously stored photographic and angiographic data on a miniature display with VGA or SVGA resolution. The miniature display is attached to a beamsplitter or a partially transmitting mirror on the second ocular of the binocular slit-lamp biomicroscope such that the graphical information is displayed registered with, and superimposed, on the real-time biomicroscopic image.

Another important aspect of the method of the invention is the real-time application of the tracking algorithm. Treatment facilitation and real-time image comparison requires rendering of stored images registered with the real-time biomicroscopic image. If there is minor movement of the head or eye resulting in a change in the biomicroscopic image, the change must be detected so that previously stored data may be re-rendered superimposed with the new illuminated image. Without such real-time updates, abnormal tissue will be incorrectly identified, e.g. abnormal tissue to undergo laser treatment will not be correctly registered with fluorescein angiography landmarks resulting in a mismatch of tissue identified with tissue actually requiring treatment.

BRIEF DESCRIPTION OF THE DRAWINGS

The foregoing and other novel features and advantages of the invention will become more apparent and more readily appreciated by those skilled in the art after consideration of the following description in conjunction with the associated drawings, of which.

DETAILED DESCRIPTION OF THE PRESENTLY PREFERRED EMBODIMENTS

A preferred embodiment of the invention will now be described in detail with reference to FIGS. 1–9. Those skilled in the art will appreciate that the description given herein with respect to those figures is for exemplary purposes only and is not intended in any way to limit the scope of the invention. All questions regarding the scope of the invention may be resolved by referring to the appended claims.

Figure 1:
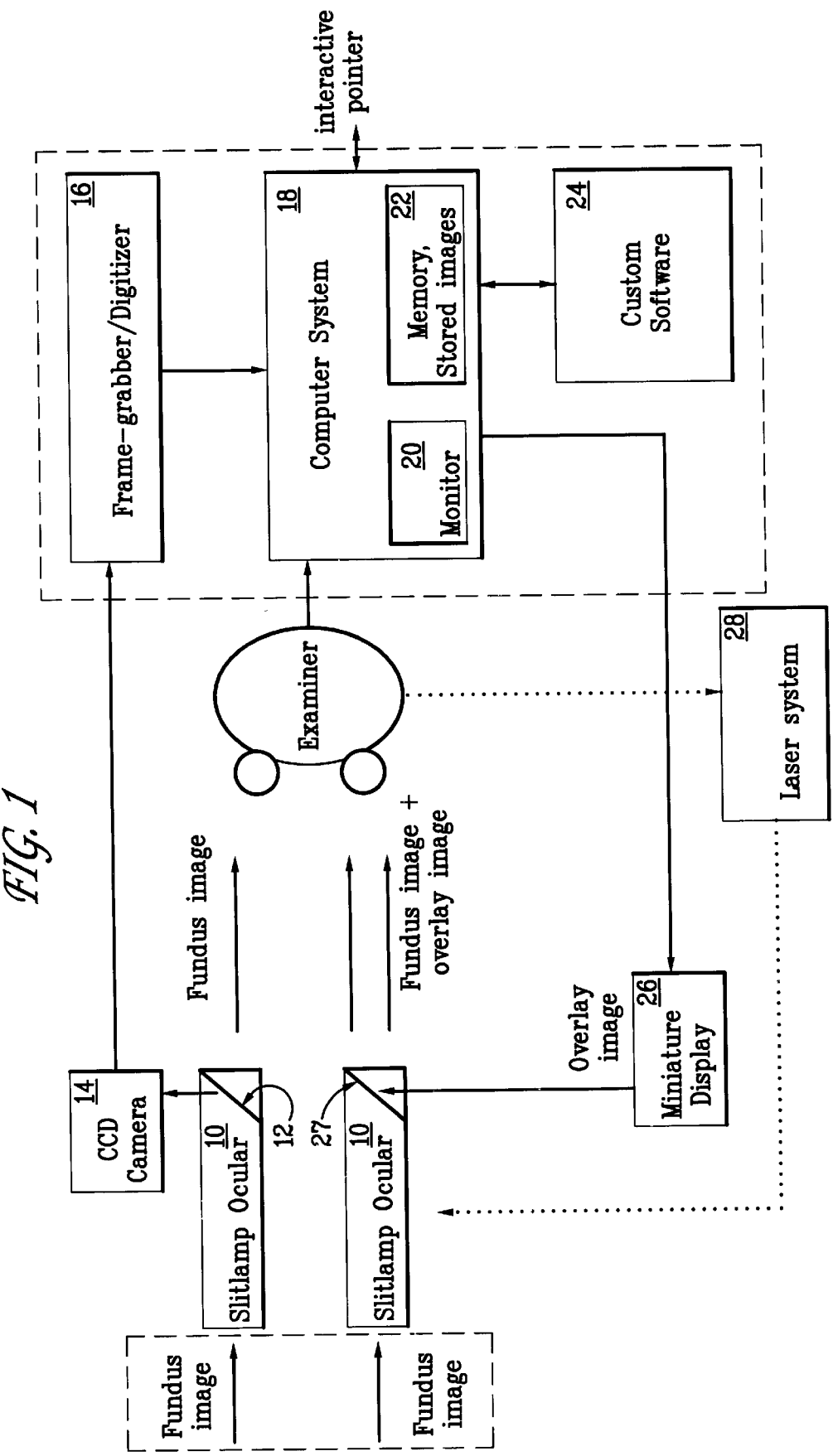
FIG. 1 is a schematic of the hardware configuration of the invention.

FIG. 1 is a schematic of the hardware configuration of the invention. As illustrated, binocular fundus images are acquired on a standard slit-lamp biomicroscope 10 permitting stereoscopic binocular imaging of the fundus by the examiner. Although the invention is described for fundus imaging, those skilled in the art will appreciate that a slit-lamp platform also facilitates an augmented reality environment for anterior segment examination as well. In addition, while the slit-lamp platform is presently preferred, functionally equivalent platforms such as the binocular indirect ophthalmoscope and the operating microscope may also be used. The system may also be built around a standard fundus camera with image acquisition and overlay through a single ocular. Those skilled in the art will appreciate that such a platform is essentially equivalent, but without the benefits of stereoscopic examination.

A portion of the slit-lamp image for one eye passes through a beamsplitter 12 to one eye of the examiner, while another portion is deflected by beamsplitter 12 to CCD camera 14 or an equivalent image capture device. Those skilled in the art will appreciate that the beamsplitter may be a partially transmitting mirror or other equivalent device. The image from the CCD camera 14 then is passed through a framegrabber/digitizer interface 16 to a computer system 18 for processing. The fundus image is acquired with the framegrabber/digitizer interface 16, which may include on-board memory without on-board signal processing as, for example, in the Matrox (Quebec, CA) Corona or Coreco (Quebec, CA) Ultra II. Greater speed may be achieved with on-board processing to include convolution, edge-detection, template matching, and the like, but acceptable speed may be achieved with software processing alone as described with respect to FIGS. 2 and 3 below. These interfaces are functionally equivalent with or without on-board image processing. On the other hand, the computer system 18 is preferably an IBM compatible PC, although Apple and Unix-based (Sun, Silicon Graphics, etc.) personal computers/workstations are functionally equivalent. As shown, the computer system 18 includes a monitor 20 and a memory 22 for storing images. Custom software 24 (FIG. 2) loaded into computer system 18 coordinates instrument function. Images are stored in memory 22 or on-board the framegrabber/digitizer board 16 and may be displayed on monitor 20. Under software control, the examiner controls the images to be rendered. The software, based on the image acquired in real-time by the CCD camera 14, registers the stored images in memory 22 and drives the miniature display 26 to overlay stored images onto the real-time biomicroscopic view in one eye using beamsplitter 27 or some other equivalent device such as a partially transmitting mirror. As will be explained in more detail below, one embodiment of the invention permits the received fundus image in one eye and the real-time fundus image plus overlay image in the other eye of the examiner to be used whereby the examiner may appropriately control laser system 28 for laser guided laser therapy.

The miniature display 26 is preferably a VGA (or better) resolution LCD, but may be replaced by small cathode ray tube (CRT) or other functionally equivalent display technology with at least VGA resolution. The computer and the framegrabber board, for example, the Matrox Corona, are able to drive both the monitor 20 and the miniature display 26. The examiner may interact with the images by mouse as visualized on the monitor 20 and/or the miniature display 26. Those skilled in the art will appreciate that functionally equivalent interactivity may be accomplished with voice recognition technology.

A straightforward extension of the embodiment of FIG. 1 is to overlay images in both eyes providing stereoscopic overlay; the principles of implementation are identical. In either case, the examiner will control the brightness of the image overlay.

In a presently preferred embodiment of the invention, laser system 28 is provided for image guided laser therapy. Laser delivery in accordance with the invention is usually slit-lamp based, and such slit-lamp-based laser systems 28 are commercially available (for example, Coherent, Inc., Palo Alto, Calif.). Accordingly, the entire embodiment of FIG. 1 may be integrated into the laser-equipped slit-lamp for image-overlay-guided laser therapy.

Figure 2:
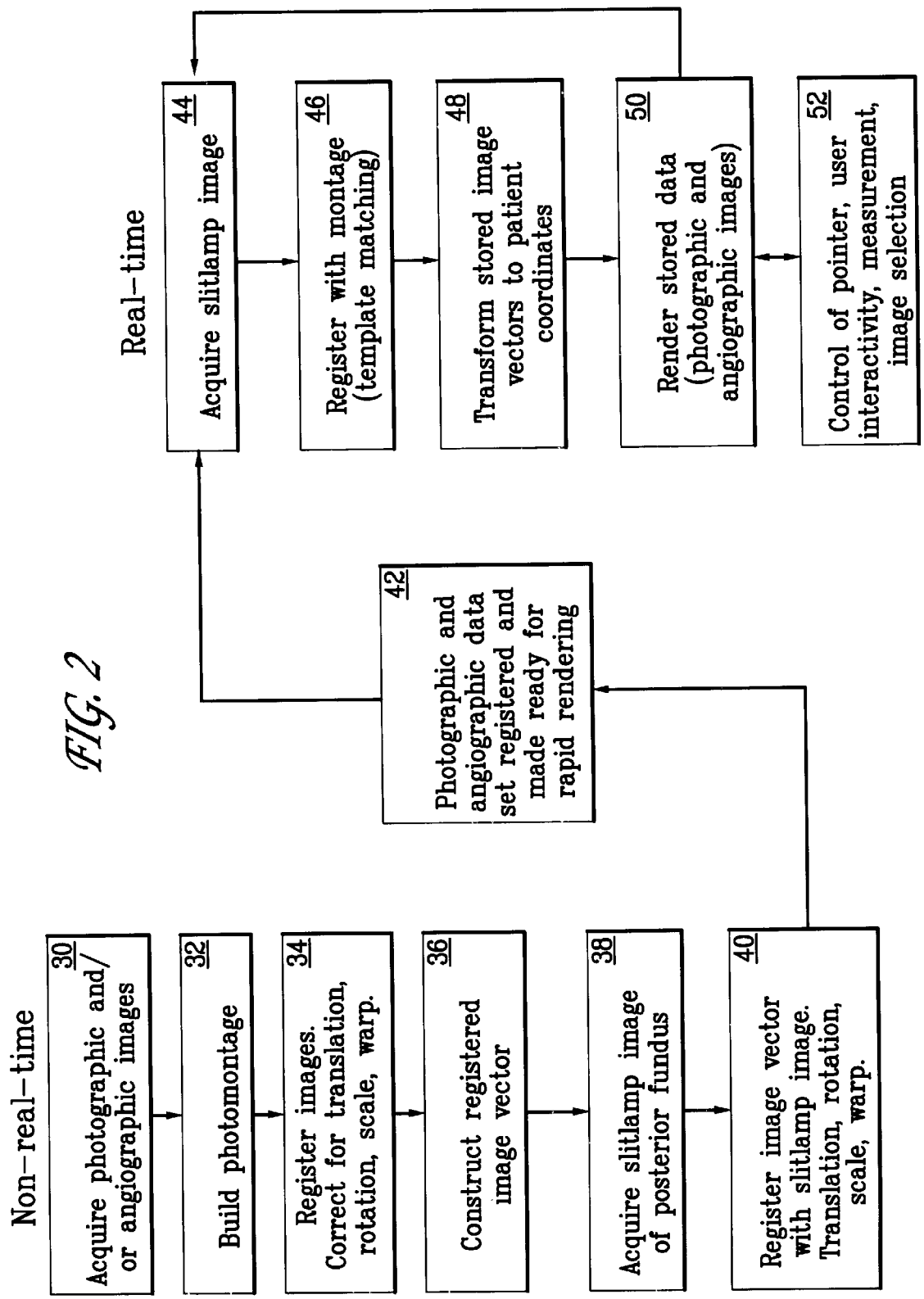
FIG. 2 is a flow diagram of the method of the invention as implemented in software.

FIG. 2 is a flow diagram of the method of the invention as implemented in software 24. As illustrated, the software 24 processed by computer system 18 is divided into non-real-time and real-time components. Generally, the aim of the non-real time component is to build a map (photomontage) for subsequent tracking and to create an image vector of angiographic and photographic images registered with high accuracy so as to be ready for rapid image rendering. On the other hand, the aim of the real-time component is to acquire the slit-lamp image, to determine the position of the illuminated image relative to the stored data (FIG. 3), to render the previously stored data overlayed on the real-time biomicroscopic image, and to permit interactive control of image selection, pointing and measurement.

As illustrated in FIG. 2, for the non-real-time component, photographic and/or angiographic images are acquired on standard fundus photography equipment (for example, Topcon Corp., Paramus, N.J.) with or without stereoscopic images. One to seven or more color or monochromatic fundus images are acquired with the fundus camera and are montaged at step 32 as described below. The images may be acquired at step 30 with either analog or digital techniques. If acquired as analog (film-based) images, the images will be first digitized with standard 35 mm slide scanners (for example, Polaroid SprintScan or Microtek Scanmaker 35tplus). As will be explained in more detail below, the current preferred embodiment for montaging at step 32 is a partial Hausdorff distance-based algorithm, although other algorithms may be developed to generate seamless, accurate image montages.

Figure 4:
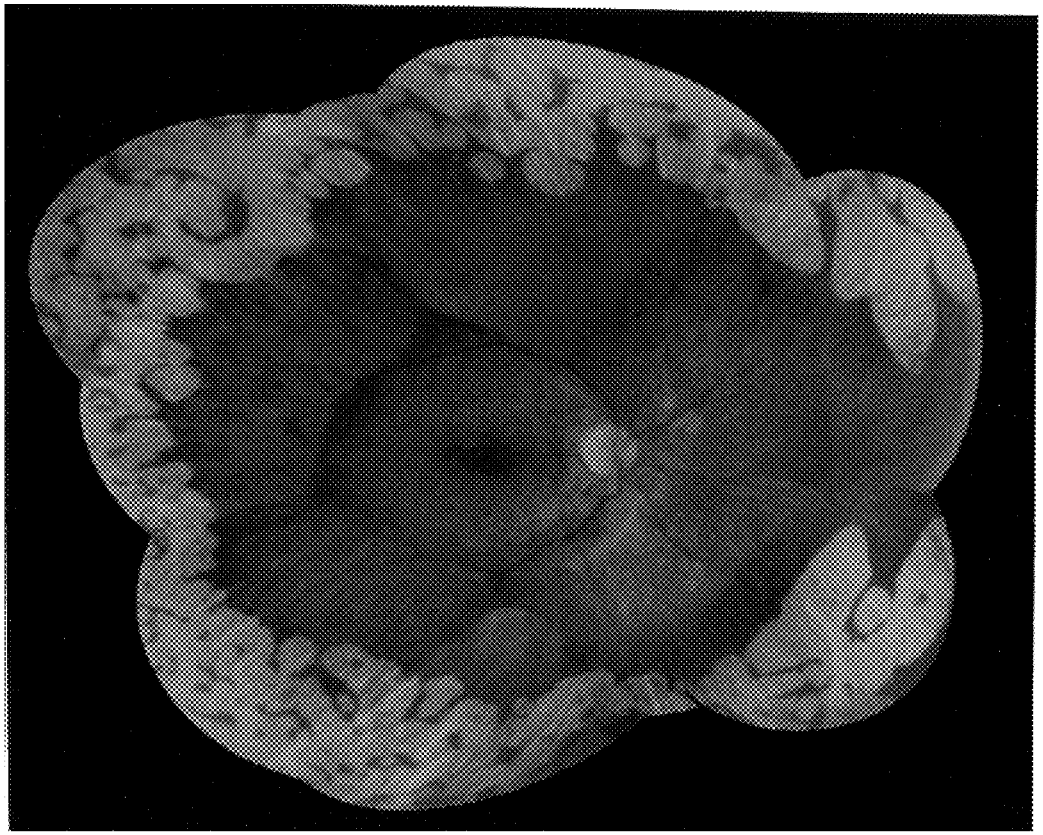
FIG. 4 illustrates a prior art photomontage of the fundus.

The current state of the art for montaging is manually-assisted montaging with noticeable seams between images. For example, FIG. 4 illustrates a montage in an article by Mahurkar et. al, *Investigative Ophthalmology and Visual Science,* September 1996, Vol. 37, No. 10, pages 1675–1683, with noticeable seams between images. These seams present in the montage yield spurious edges which corrupt the performance of edge-based tracking and are undesirable. The technique of the invention thus includes an automated method for seamless montaging.

The "Hausdorff distance" technique described by Huttenlocher et al. in an article entitled "Comparing Images Using the Hausdorff Distance," *IEEE Trans. Patt. Anal. Mach. Intell.,* Vol. 15, pp. 850–863, 1993, and by Rucklidge in an article entitled "Locating Objects Using the Hausdorff Distance," *Proc. IEEE Int. Conf. Computer Vision,* pp. 457–464, 1995, is well-suited for registration and montaging functions in accordance with the invention since that technique (a) runs well for edge-detected images, (b) tolerates errors as well as the presence of extra or missing data points between data sets, and (c) operates on an arbitrary, user-defined transformation function. Accordingly, the Hausdorff distance technique is utilized in accordance with the invention with variable scale, translation, and rotation to build a photomontage and to register the images corrected for translation, rotation, scale, and warp.

The Hausdorff distance is computed only for positively thresholded (e.g. edge-detected) points and is defined by $$H(A, B) = \max(h(A,B), h(B,A))$$

$$h(A,B) = \max_{a \in A} \min_{b \in B} \|a-b\|$$

where $\|a-b\|$ represents Euclidean distance.

The Hausdorff distance identifies the point $a \in A$ that is farthest from any point of B, and measures the distance from a to its nearest neighbor in B. Equivalently, if $H(A, B)=d$, then $$\forall a \in A, \exists b \in B \ni \|a-b\| \leq d$$

or all points in A must be within a distance d from some point in B, with the most mismatched point at exactly a distance d from the nearest point in B.

Due to occlusion and outliers, not all points in A will have a meaningful correspondence with a point in B. The partial Hausdorff distance measure is thus used:

$$H_K(A,B) = \max(h_K(A,B), h_K(B,A))$$

$$h_K(A,B) = K^{th} \min \|a-b\|$$

$$a \in A \ b \in B$$

An extension of the Hausdorff distance by Huttenlocher et al. defines a fraction of points in set A that lie within $\in$ of some point in B:

$$F_\epsilon(A, B) = \min(f_\epsilon(A, B), f_\epsilon(B, A))$$

$$f_\epsilon(A, B) = \frac{\#(A \wedge B^\epsilon)}{\#(A)}$$

where $B^\in$ is the point set B dilated by $\in$, or the Minkowski sum of B with a disk of radius $\in$. In other words, f(A,B) is the fraction of points in A that lie within $\in$ of some point in B. Instead of fixing K and minimizing $H_K(A,B)$, the dilation $\in$ is fixed and F(A,B) is maximized.

Huttenlocher et al. present an algorithm in the aforementioned article for efficient computation of image matching based on Hausdorff distance for discretized, binarized images. When compared with correlation methods, their algorithm was more accurate, more robust, and more efficient. The present inventors have demonstrated the suitability of this approach for the present application. In particular, the inventors have implemented a modified, bidirectional Hausdorff-distance-based approach for image montaging.

The montaging method of the invention comprises the steps of acquiring multiple, partially overlapping fundus images. The images are then smoothed and edge detected, for example, using the techniques disclosed by Canny in an article entitled "A Computation Approach to Edge Detection," *IEEE Trans. Pat. Anal. Mach. Intel.,* Vol. 8, pp. 34–43, 1986. To match two images together, the maximum Hausdorff fraction over translation, rotation, and scale is found. Given that the fundus images only partially overlap, if all points in both images are used in the Hausdorff fraction calculation, then the resulting fraction will be very low. In fact, it is likely that a random transformation where the fundus images have more overlap will have a larger fraction if all points are considered.

Therefore, when computing the Hausdorff fraction F(A, B) for a given transformation, A and B are the sets of points from the two images that are in the overlap region of the images. All points that fall outside the overlap region for a certain transformation are ignored. To prevent a false match with a high fraction where only a very small percentage of points lie within the overlap region, a minimum percentage of image points (currently 10%) must lie in the overlap region for the transformation to be considered a possible match.

To build the photomontage, the position and scale of all images must be determined relative to a fixed coordinate system (that of the montage). Under the current design, a "central" image is chosen a priori by the user, and the coordinate system of this image is used for the montage. Generally, the "central" image is easily identifiable by the user because it contains both the fovea (which should be approximately centered) and the optic nerve. All the other images are then matched to the central image, yielding a transformation that maximizes the partial Hausdorff fraction.

All images that match the central image with a partial Hausdorff fraction above some threshold (currently 70%) are considered to be correctly placed in the montage. Any images that do not match the central image are then matched against the other images.

Once the positions and scales of all the images are known relative to the central image, the montage image can be built at step 32. One simple method of building the montage is to average the intensity values of the overlapping images at every pixel. The montage image, I, is computed as follows:

$$I(x, y) = \frac{\sum_{i=1}^{N} (\delta_i(x, y) \times I_i(x, y))}{\sum_{i=1}^{N} \delta_i(x, y)}$$

where $\delta_i(x,y)$ is 1 if (x,y) lies inside image I and 0 otherwise.

However, in general, the average intensities of the images are not equal, so edge artifacts are introduced at the image borders. Furthermore, the average intensity in any one image generally varies over the image. The fundus images are often brighter near the center and lose brightness and contrast near the image borders. The vessels used as landmarks disappear near the image borders. Thus, in addition to the edge artifacts, simply averaging images also degrades the visibility of the vessels in the montage near image borders.

Therefore, when blending all the images to form the montage, a convex combination is used that puts a greater weight on pixels closer to the center of an image:

$$I(x, y) = \frac{\sum_{i=1}^{N} (d_i^2(x, y) \times I_i(x, y))}{\sum_{i=1}^{N} d_i^2(x, y)}$$

where $d_i$ is the distance from the point (x,y) to the nearest border of image i if (x,y) is inside the image, and 0 if (x,y) is outside the image. This blending removes many of the artifacts due to varying contrast and intensity.

Figure 5A:
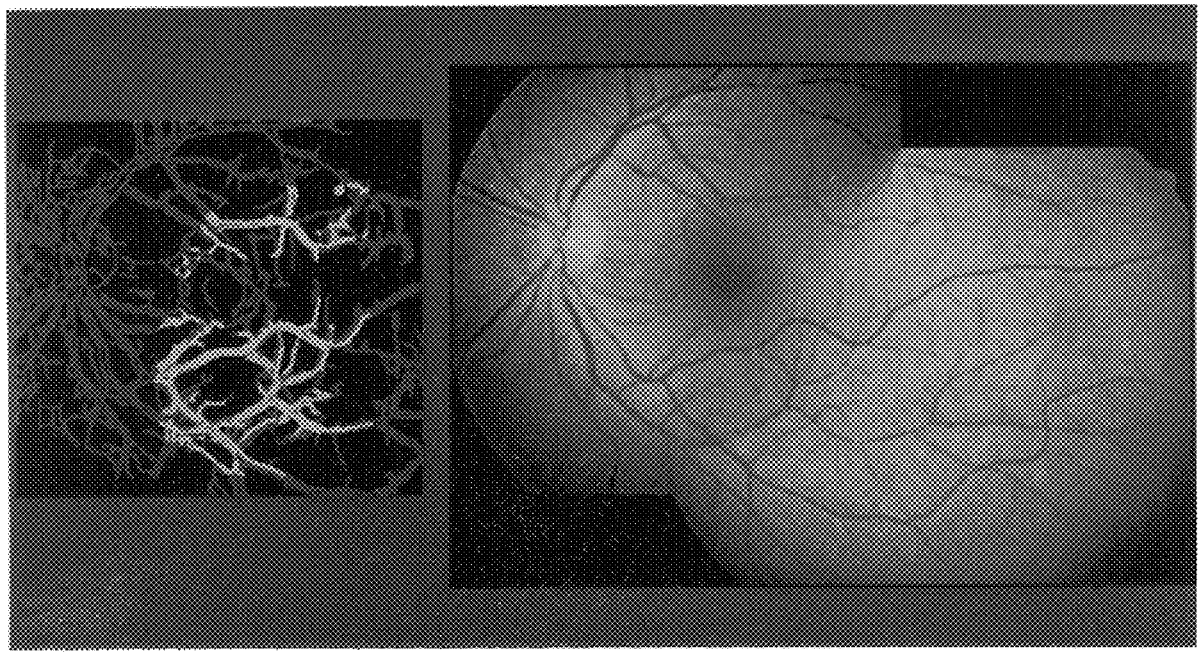
FIGS. 5A and 5B illustrate example matches in montage building in accordance with the invention.
Figure 5B:
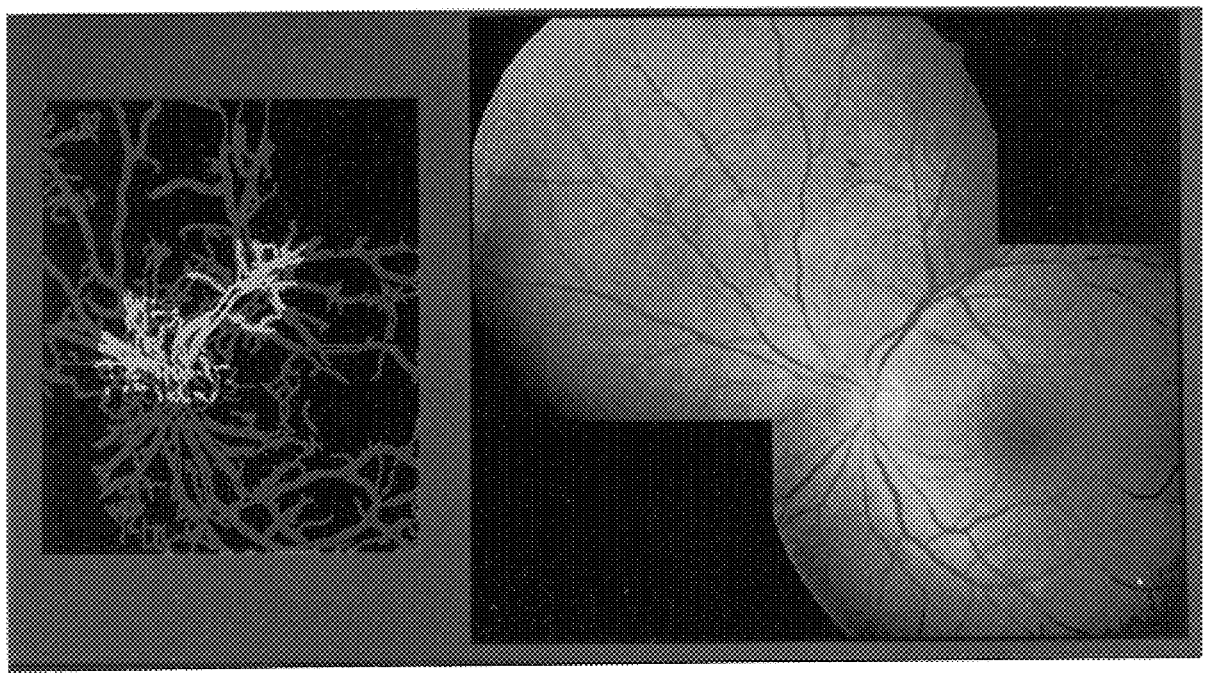
Figure 6:
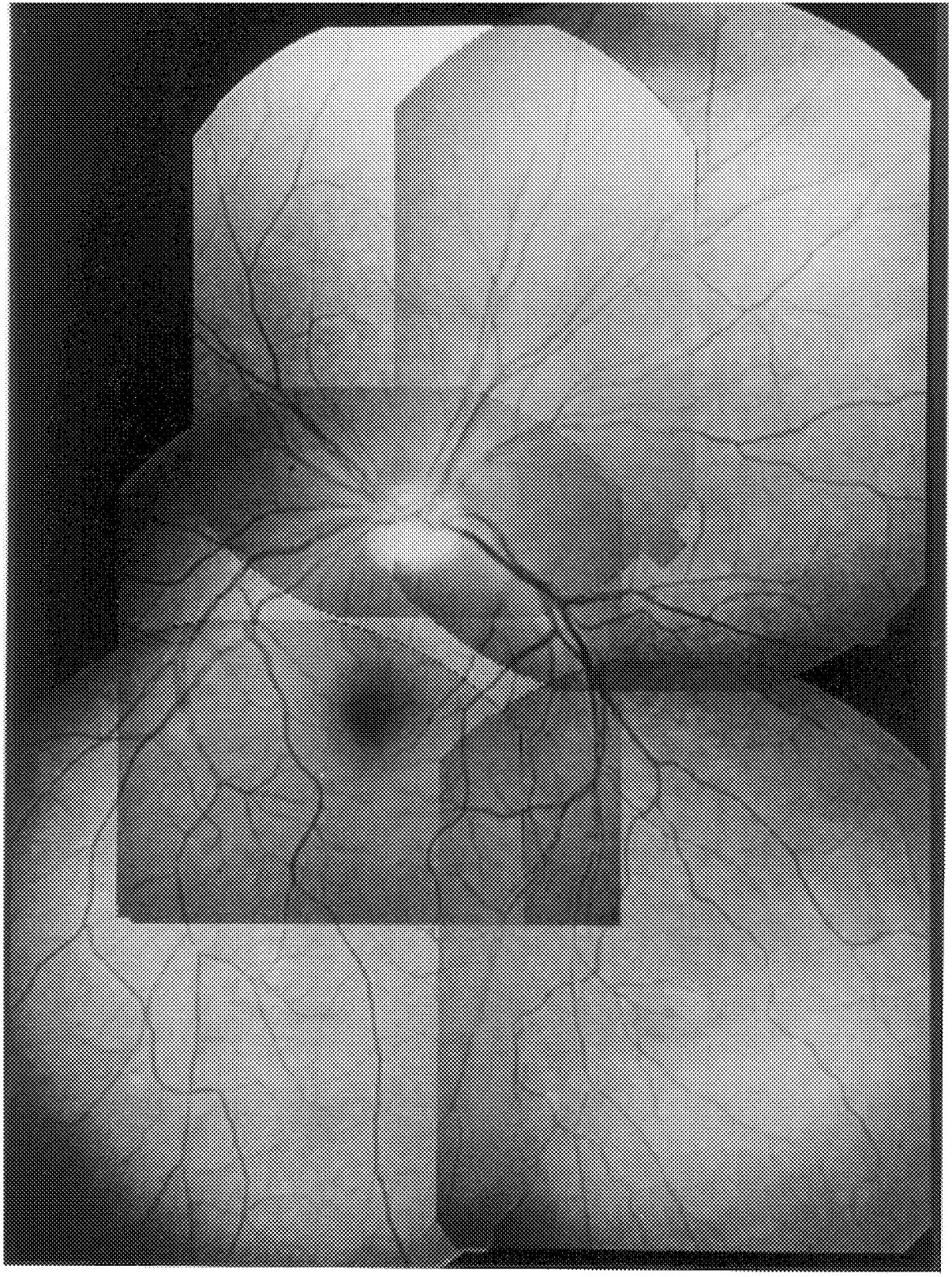
FIG. 6 illustrates a montage developed using the techniques of the invention before smoothing.
Figure 7:
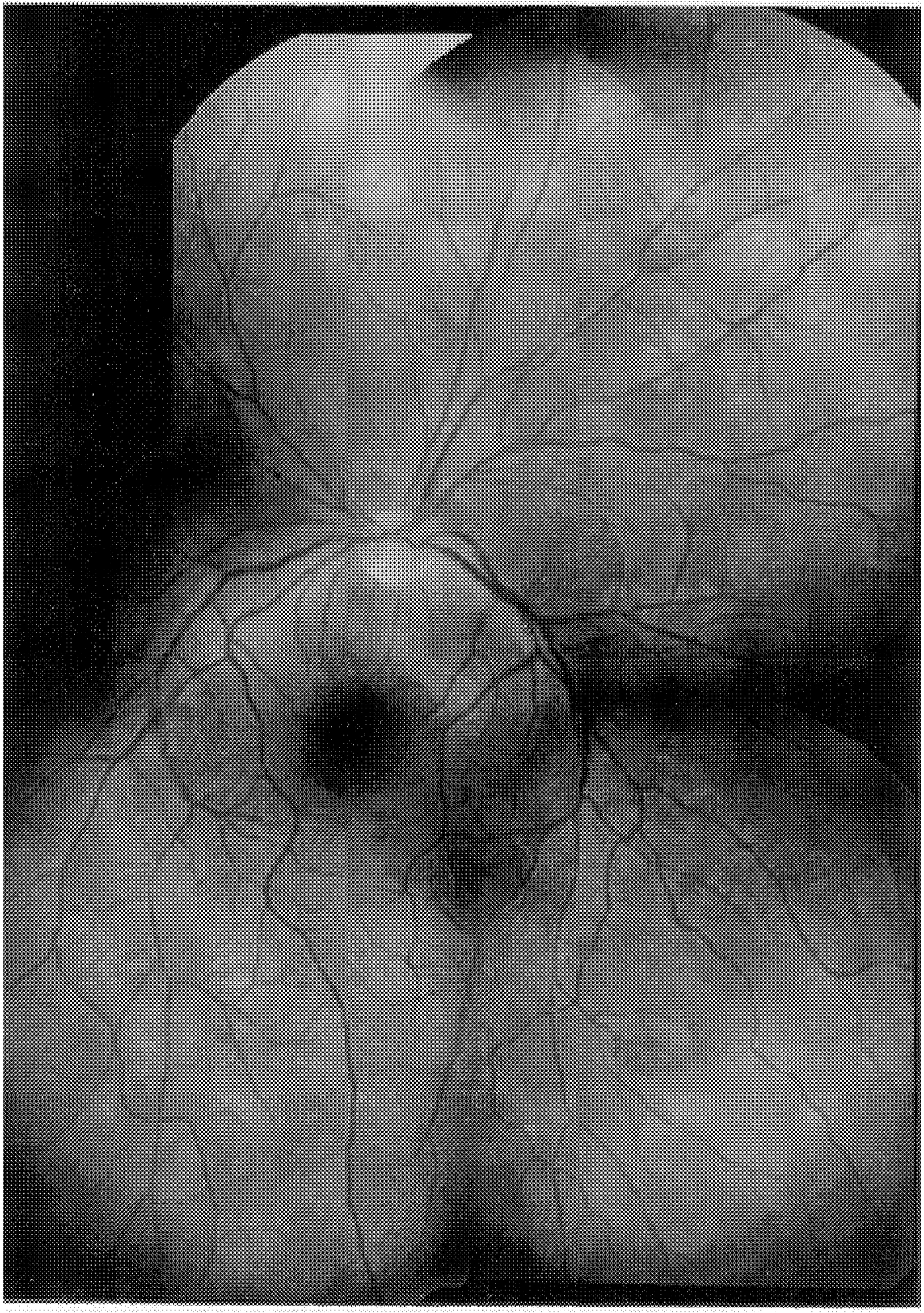
FIG. 7 illustrates the montage of FIG. 6 after smoothing.

FIGS. 5A and 5B show two example matches with smoothing, while FIG. 6 shows the result of montaging five distinct, partially overlapping fundus images, without smoothing. Obvious seams are noted in the montage. FIG. 7 shows the five images of FIG. 6 following montaging and smoothing in accordance with the invention, essentially without seams between overlapping images.

Next, the stored angiographic and photographic images are registered with the photomontage with high accuracy at step 34. The preferred embodiment of the invention uses Hausdorff distance based algorithms or standard polynomial based image warping techniques as available in Interactive Data Language (IDL) 5.0 (Boulder, Co.) for this purpose. The inventors have similarly applied elastic-matching techniques. A registered image vector is then constructed and stored at step 36.

Also, in order to allow for maximum real-time speed, a single image of the posterior fundus is acquired at step 38 with the slit lamp instrument 10 using a wide illumination. The stored image vector (built on images acquired on other fundus imaging platforms—specifically, fundus cameras) is then registered at step 40 with this slit-lamp-derived image correcting for translation, rotation, scale, and warp-related image misalignment. Again, Hausdorff-distance, elastic matching, and polynomial warping algorithms are effective, with the latter representing the currently preferred embodiment. The photographic and angiographic data set is thus registered with high accuracy and prepared at step 42 for rapid rendering.

The system is now prepared for real-time function. A patient is seated at the slit-lamp 10, and a narrow image 45 (FIG. 3) is acquired at step 44. Algorithms for real-time retinal tracking for automated laser therapy may be used as described by Markow et al. in an article entitled "Real-time Algorithm for Retinal Tracking," *IEEE Trans. Biomed. Engineering,* Vol 40, pp. 1269–1281, 1993; by Barrett et al. in an article entitled "Digital Tracking and Control of Retinal Images," *Optical Engineering,* Vol. 33, pp. 150–159, 1994; by Barrett et al. in an article entitled "Computer-aided Retinal Photocoagulation System," *J. Biomedical Optics,* Vol. 1, pp. 83–91, 1996; and by Becker et al. in an article entitled "Real-time Image Processing Algorithms for an Automated Retinal Laser Surgery System," *Proc. IEEE 2nd Int. Conf. Image Proc.,* pp. 426–429, 1995. However, such tracking algorithms require multiple templates to follow retinal vessels at several fundus locations and therefore require a large illumination area. In addition, tracked vessels must be visible at all times, which is not consistent with the inventors' goal to allow for narrow beam illumination, and is more suitable for a fundus camera with monocular, wide angle viewing. Further, these prior art tracking algorithms limit the search to a small area surrounding the previously tracked position and are not tolerant of large changes in fundus position as might be encountered during a slit-lamp fundus, biomicroscopic examination.

Figure 3:
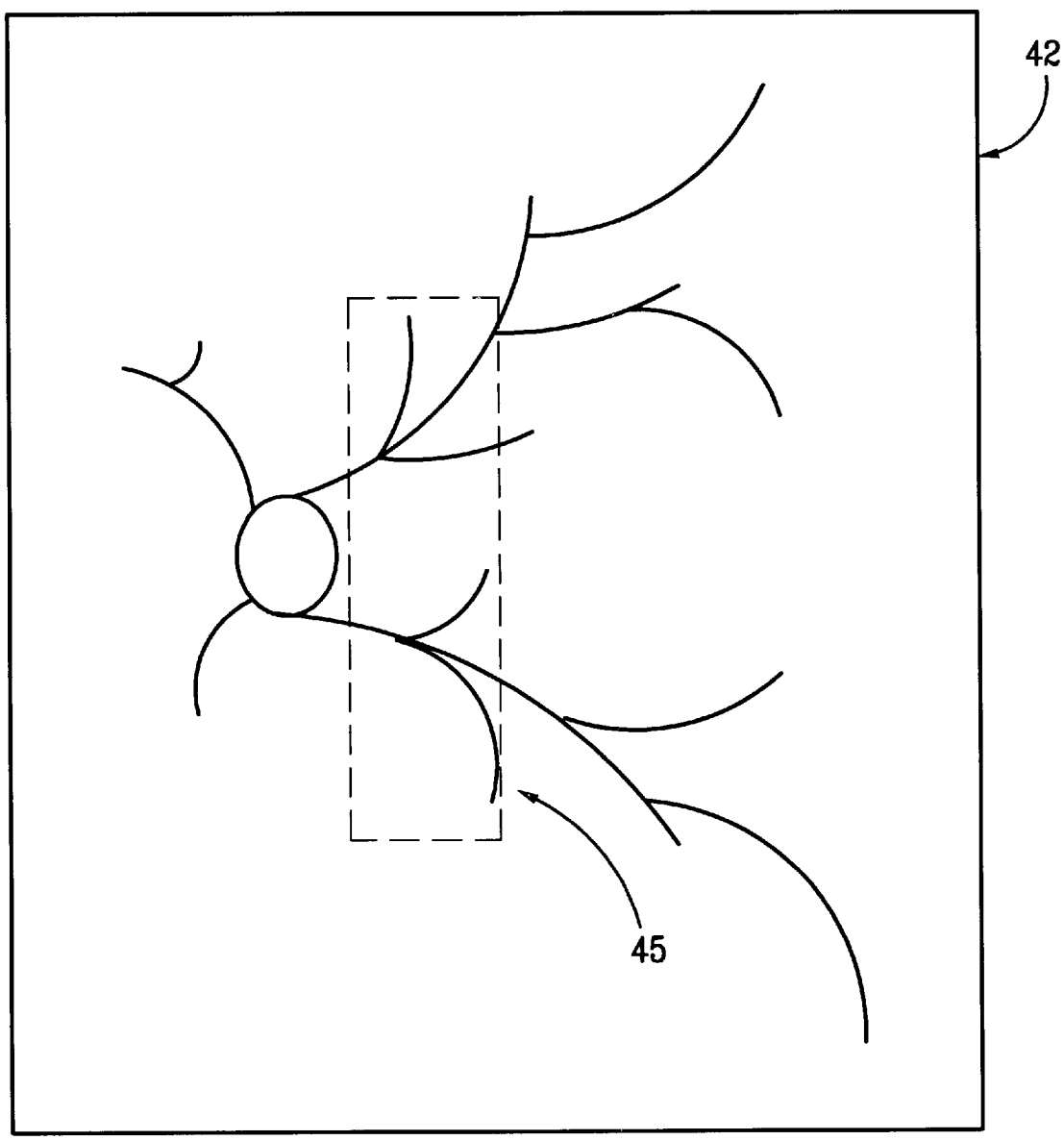
FIG. 3 illustrates template matching of the slit-beam image with the montage image.

The narrow slit-lamp image acquired at step 44 is then registered with the previously stored montage using template matching algorithms at step 46. As shown in FIG. 3, the schematized depiction of the posterior fundus features (montage) 42 is registered using template matching with the slit-beam image 45 acquired in real-time at step 44. The currently preferred embodiment uses commercially available software from Matrox (MIL 5.0, Quebec, CA) for template matching. Other similar software such as LogicalVision WiT (Burnaby, British Columbia) is functionally equivalent and can also be used. In addition, template matching may be accomplished with processing on the board of the framegrabber 16 using dedicated hardware or software controlled by on board digital signal processing (DSP) or equivalent technologies as on the Matrox Genesis, Coreco Cobra, and many other commercial products. Template matching may also be accomplished with an optical correlator (for example, Physical Optics, Torrance, Calif., and other similar technologies). Those skilled in the art will appreciate that these methods are functionally equivalent to software-based template matching.

The stored image vector may then be transformed to the live-fundus-image based coordinate system of the patient at step 48. In the currently preferred embodiment, the vectors are translated only with MIL 5.0. Prior, non-real-time, highly accurate warping of the image vector to the slit-lamp acquired fundus image allows for accurate image mapping, but rotation and more complex image transformations may be incorporated as processing speeds increase, or dedicated hardware allows fast image vector transformation. The photographic and/or angiographic images are then rendered at step 50.

Figure 8B:
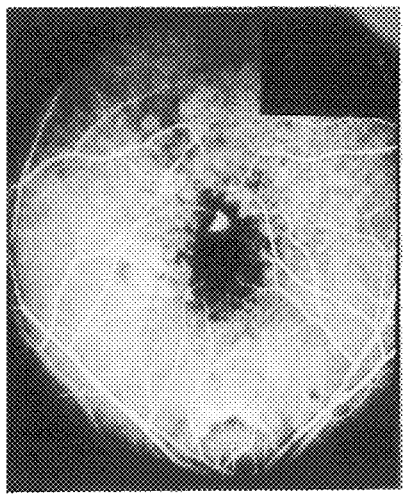
FIGS. 8A and 8B respectively illustrate a fundus photograph and a fluorescein angiographic image of a patient with a sickle shaped area of new blood vessels just to the right (temporal) of the fovea.
Figure 8A:
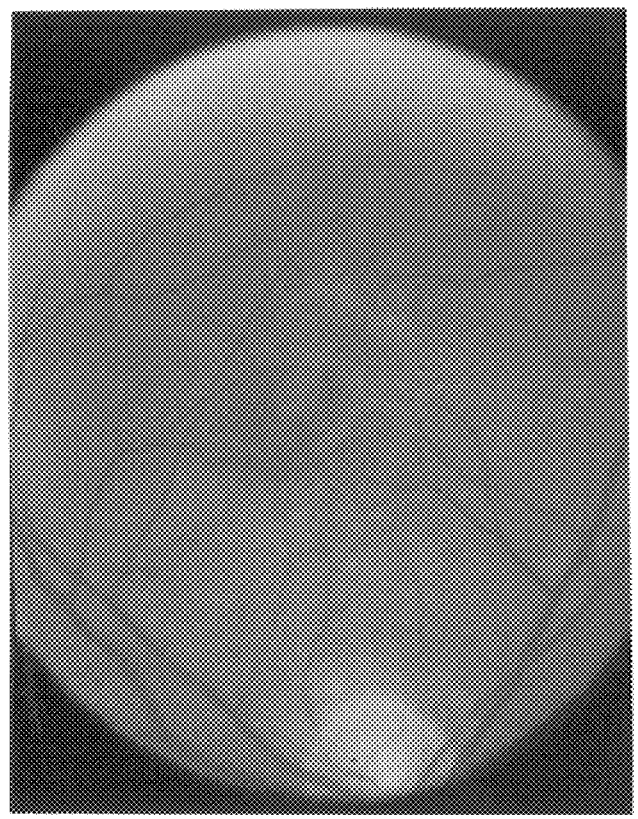
Figure 9:
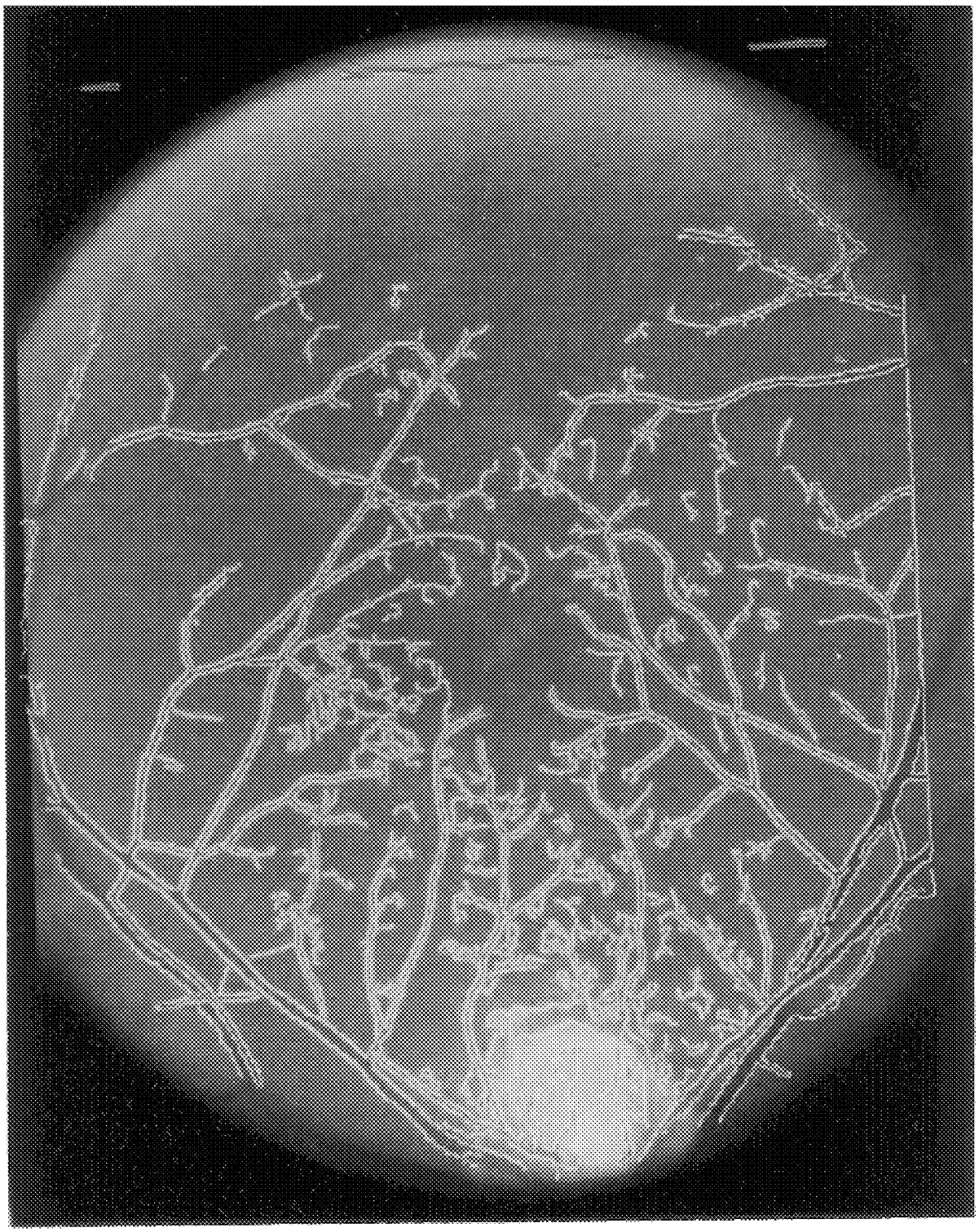
FIG. 9 illustrates an overlay of edge information from the angiographic image in FIG. 8B onto the fundus photograph of FIG. 8A, whereby the new blood vessels are readily identified in this augmented reality depiction.

FIGS. 8A and 8B respectively illustrate a fundus photograph and a fluorescein angiographic image of a patient with a sickle shaped area of new blood vessels just to the right (temporal) of the fovea. The new blood vessels cannot be discerned on the fundus photograph of FIG. 8A, but are readily visible on the fluorescein angiogram of FIG. 8B. FIG. 9 illustrates an overlay of edge information from the angiographic image in FIG. 8B onto the fundus photograph of FIG. 8A, whereby the new blood vessels are readily identified in this augmented reality depiction, thereby demonstrating the utility of image overlay in accordance with the invention. Edge information from the angiographic image in FIG. 8B is also superimposed onto the image of FIG. 9. The new blood vessels are readily identified in this augmented depiction.

At step 52, the examiner and/or a remote observer (e.g., an expert supervising the local examiner, or a trainee "observing" a diagnostic or therapeutic maneuver) will be able to view a real-time graphical display of the biomicroscopic image, and will be able to communicate questions or recommendations by text or voice. The software 24 thus allows the examiner and/or a remote observer to control a mouse-based "virtual pointer" to unambiguously identify regions of interest. Of course, other known pointing methods may be used as well. The image created by the pointer, for example, the lines created and areas demarcated on the real-time image, are rendered at a known position relative to ocular landmarks as determined by computer system 18. Identical algorithms for overlay of previously stored photographic and angiographic images may then be applied to the image created by the pointer. The position of the pointer image may then be registered with the real-time fundus image and the photomontage using template matching or functionally equivalent methods as in step 46, transformed to patient coordinates as in step 48, and rendered as in step 50, thereby allowing for real-time update and overlay of the pointer image and facilitating real-time image measurement and analysis whereby the markings placed on the eye move with the eye. Length and area measurements are computed and displayed with commercially available, real-time software, for example, Matrox Imaging Library in the text window of monitor 20 or miniature display 26. By allowing a local and a remote observer to control the pointer so as to enable distance and area measurements in this fashion, and by allowing the examiner and remote observer to communicate by voice or text, interactivity for telecollaboration, telemedicine, teaching, and the like, is facilitated.

As noted above, a laser system 28 may be incorporated for image guided laser therapy. Since laser delivery is usually slit-lamp based, the entire invention may be integrated into a laser-equipped slit-lamp for image-overlay-guided laser therapy.

Although several embodiments of the invention have been described in detail above, those skilled in the art will appreciate that numerous other modifications to the invention are possible within the scope of the invention. Accordingly, the scope of the invention is not intended to be limited to the preferred embodiments described above, but only by the appended claims.

We claim:

1. A method for implementing an ophthalmic augmented reality environment for overlaying at least one of previously stored photographic and angiographic images onto a real-time ophthalmic image, comprising the steps of:
    acquiring a real-time image of the eye;
    registering landmarks of said acquired real-time image of the eye with at least one of said at least one previously stored photographic and angiographic images; and
    displaying said at least one of said at least one previously stored photographic and angiographic images overlayed over said real-time image.

2. A method as in claim 1, wherein said real-time image acquiring step comprises the step of taking a real-time image through a slit-lamp biomicroscope and said displaying step comprises the step of overlaying said at least one of said at least one previously stored photographic and angiographic images over said real-time image through at least one ocular of said slit-lamp biomicroscope.

3. A method as in claim 2, wherein said overlaying step comprises the step of adding said at least one of said at least one previously stored photographic and angiographic images to said real-time image using a beamsplitter of said slit-lamp.

4. A method as in claim 1, wherein said real-time image acquiring step comprises the step of taking a real-time image through one of an operating microscope and indirect ophthalmoscope and said displaying step comprises the step of overlaying said at least one of said at least one previously stored photographic and angiographic images over said real-time image through at least one ocular of said one of said operating microscope and said indirect ophthalmoscope.

5. A method as in claim 4, wherein said overlaying step comprises the step of adding said at least one of said at least one previously stored photographic and angiographic images to said real-time image using a beamsplitter of said one of said operating microscope and said indirect ophthalmoscope.

6. A method as in claim 1, wherein said real-time image acquiring step comprises the step of taking a real-time image through a fundus camera and said displaying step comprises the step of overlaying said at least one of said at least one previously stored photographic and angiographic images over said real-time image through an ocular of said fundus camera.

7. A method as in claim 6, wherein said overlaying step comprises the step of adding said at least one of said at least one previously stored photographic and angiographic images to said real-time image using a beamsplitter of said fundus camera.

8. A method as in claim 1, wherein said registering step comprises the step of matching a template of said acquired real-time image of the eye with a template of said at least one of said at least one previously stored photographic and angiographic images.

9. A method as in claim 1, comprising the additional steps of generating a seamless photomontage of said at least one previously stored photographic images and registering said photomontage with a slit-lamp image of said eye prior to said real-time image acquiring step.

10. A method as in claim 9, wherein said photomontage generating step comprises the steps of:
    acquiring multiple, partially overlapping images of the eye; and
    matching two eye images together by finding a maximum partial Hausdorff distance fraction over at least one of translation, rotation, and scale of sets of points of said two eye images which are in an overlap region of said two eye images.

11. A method as in claim 10, comprising the additional step of weighting pixels in eye images to be included in said photomontage with a convex weighting such that pixels near the center of said photomontage have greater weight than pixels around the periphery of said photomontage.

12. A method as in claim 1, comprising the additional step of providing remote control of selection of the real-time image to be acquired in said acquiring step.

13. A method of generating a seamless photomontage of photographic images of the eye, comprising the steps of:
    acquiring multiple, partially overlapping photographic images of the eye;
    matching two eye images together by finding a maximum partial Hausdorff distance fraction over at least one of translation, rotation, and scale of sets of points of said two eye images which are in an overlap region of said two eye images; and
    weighting pixels in eye images to be included in said photomontage with a convex weighting such that pixels near the center of said photomontage have greater weight than pixels around the periphery of said photomontage.

14. A method as in claim 13, comprising the additional step of determining whether a predetermined minimum percentage of image points are present in said overlap region of said two eye images prior to said matching step.

15. A method of providing laser guided image therapy using an ophthalmic augmented reality environment for overlaying at least one of previously stored photographic and angiographic images onto a real-time ophthalmic image, comprising the steps of:
    acquiring a real-time image of the eye;
    registering landmarks of said acquired real-time image of the eye with at least one of said at least one previously stored photographic and angiographic images;
    displaying an augmented reality image including said at least one of said at least one previously stored photographic and angiographic images overlayed over said real-time image; and
    guiding a laser during laser therapy of the eye using said augmented reality image.

16. A method for real-time measurement and analysis of ophthalmic images, comprising the steps of:
    acquiring and capturing a real-time ophthalmic image;
    displaying the captured real-time ophthalmic image to an observer;

drawing on the real-time image with an interactive pointer device to create a drawn image;

registering said captured real-time ophthalmic image with said drawn image; and displaying said drawn image registered with, and overlayed on, said real-time ophthalmic image.

17. A method as in claim 16, wherein said registering step comprises the step of registering said drawn image with at least one of previously stored photographic and angiographic images and said displaying step comprises the step of displaying said drawn image registered with, and overlayed on, said at least one of said at least one previously stored photographic and angiographic images.

18. A method as in claim 16, comprising the additional steps of computing and displaying measurement data of said real-time ophthalmic image.

19. A system which implements an ophthalmic augmented reality environment for overlaying at least one of previously stored photographic and angiographic images onto a real-time ophthalmic image, comprising:

an eye imaging device which acquires a real-time image of the eye for presentation to an examiner;

an image capturing device which captures said real-time image of the eye;

a processing device which registers landmarks of said captured real-time image of the eye with at least one of said at least one previously stored photographic and angiographic images; and an image adder which overlays said at least one of said at least one previously stored photographic and angiographic images over said captured real-time image for presentation to the examiner.

20. A system as in claim 19, wherein said eye imaging device comprises a slit-lamp biomicroscope and said image adder comprises a beamsplitter in at least one ocular of said slit-lamp biomicroscope.

21. A system as in claim 19, wherein said eye imaging device comprises one of an operating microscope and an indirect ophthalmoscope and said image adder comprises a beamsplitter in at least one ocular of said one of said operating microscope and indirect ophthalmoscope.

22. A system as in claim 19, wherein said eye imaging device comprises a fundus camera and said image adder comprises a beamsplitter in said fundus camera.

23. A system as in claim 19, wherein said image capturing device comprises a CCD camera.

24. A system as in claim 19, wherein said processing device comprises a framegrabber/digitizer which digitized frames of images from said image capturing device and a memory which stores said photographic and angiographic images.

25. A system as in claim 19, wherein said processing device comprises software which builds a seamless photomontage of said at least one previously stored photographic images and registers said photomontage with an image from a patient's eye.

26. A system as in claim 25, wherein said software builds said photomontage by controlling said processing device to perform the following steps:

acquiring multiple, partially overlapping images of the eye; and matching two eye images together by finding a maximum partial Hausdorff distance fraction over at least one of translation, rotation, and scale of sets of points of said two eye images which are in an overlap region of said two eye images.

27. A system as in claim 26, wherein said software builds said photomontage by controlling said processing device to perform the additional step of weighting pixels in eye images to be included in said photomontage with a convex weighting such that pixels near the center of said photomontage have greater weight than pixels around the periphery of said photomontage.

28. A system as in claim 19, wherein said processing device comprises software which determines the position of the captured real-time image of the eye relative to said at least one of said at least one previously stored photographic and angiographic images.

29. A system as in claim 19, wherein said processing device comprises software which renders said at least one of said at least one previously stored photographic and angiographic images overlayed on the real-time biomicroscopic image.

30. A system as in claim 19, wherein said processing device comprises software which permits interactive control of at least one of image selection, pointing, and measurement by an examiner.

31. A system as in claim 30, wherein said software further provides remote control of said at least one of said image selection, pointing, and measurement by a remote examiner.

32. A laser guided image therapy system which implements an ophthalmic augmented reality environment for overlaying at least one of previously stored photographic and angiographic images onto a real-time ophthalmic image, comprising:

an eye imaging device which acquires a real-time image of the eye for presentation to an examiner;

an image capturing device which captures said real-time image of the eye;

a processing device which registers landmarks of said captured real-time image of the eye with at least one of said at least one previously stored photographic and angiographic images;

an image adder which overlays said at least one of said at least one previously stored photographic and angiographic images over said captured real-time image for presentation to the examiner as an augmented reality image; and a laser system controlled in response to said augmented reality image.

33. A system for real-time measurement and analysis of ophthalmic images, comprising:

an eye imaging device which acquires a real-time image of the eye for presentation to an examiner;

an image capturing device which captures said real-time image of the eye;

an interactive pointer device which permits the examiner to draw on the real-time image to create a drawn image;

a processing device which registers landmarks of said captured real-time image of the eye with said drawn image;

an image adder which overlays said drawn image registered with, and overlayed on, said captured real-time image for presentation to the examiner.

34. A system as in claim 33, wherein said processing device further registers said drawn image with at least one of previously stored photographic and angiographic images and said image adder overlays said drawn image on, and registered with, said at least one of said at least one previously stored photographic and angiographic images.

35. A system as in claim 33, wherein said processing device further computes measurement data of said real-time ophthalmic image.

* * * * *